US008329211B2

(12) United States Patent
Moloye-Olabisi et al.

(10) Patent No.: US 8,329,211 B2
(45) Date of Patent: Dec. 11, 2012

(54) REINFORCED ABSORBABLE MULTI-LAYERED FABRIC FOR HEMOSTATIC APPLICATIONS

(75) Inventors: Olajompo Moloye-Olabisi, Neshanic Station, NJ (US); Dhanuraj S. Shetty, Jersey City, NJ (US); Robert W. Van Holten, Flemington, NJ (US); Degang Zhong, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 390 days.

(21) Appl. No.: 12/781,235

(22) Filed: May 17, 2010

(65) Prior Publication Data

US 2011/0282364 A1 Nov. 17, 2011

(51) Int. Cl.
*A61F 2/00* (2006.01)
*A61F 13/00* (2006.01)
*A61L 15/16* (2006.01)
*A61K 38/00* (2006.01)
*A61K 38/36* (2006.01)
*A61K 47/30* (2006.01)

(52) U.S. Cl. ........ 424/444; 424/426; 424/443; 424/447; 428/215; 428/218; 514/13.5; 514/13.6; 514/13.7; 514/13.8; 514/14.7; 514/772; 602/45; 602/60; 606/908

(58) Field of Classification Search ........................ None
See application file for complete search history.

(56) References Cited

U.S. PATENT DOCUMENTS

| 4,626,253 | A | 12/1986 | Broadmax, Jr. |
| 5,593,441 | A | 1/1997 | Lichtenstein et al. |
| 5,686,090 | A | 11/1997 | Schilder et al. |
| 7,666,803 | B2 | 2/2010 | Shetty et al. |
| 2006/0084930 | A1 | 4/2006 | Dhanaraj et al. |
| 2007/0225631 | A1 | 9/2007 | Bowlin et al. |
| 2008/0200890 | A1 | 8/2008 | Wood et al. |

OTHER PUBLICATIONS

Holcomb, J.B. et al., 'Dry Fibrin Sealant Dressings Reduce Blood Loss, Resuscitation Volume and Improve Survival in Hypothermic Coagulopathic Swine with Grade V Liver Injuries', J. Trauma, (1999) 47(2) pp. 233-242.
Holcomb, J.B. et al., 'Efficacy of a Dry Fibrin Sealant Dressing for Hemorrhage Control After Ballistic Injury', Arch Surg., (1998) 133: pp. 32-35.
Holcomb, J.B. et al., 'Implications of New Dry Fibrin Sealant Technology for Trauma Surgery', Surg. Clin. North Am., (1997) 77(4) pp. 943-952.

*Primary Examiner* — Ernst Arnold
(74) *Attorney, Agent, or Firm* — David R. Crichton

(57) ABSTRACT

The present invention is directed to a synthetic fabric comprising a multi-layered nonwoven fabric made from staples of a polyglycolide/polylactide copolymer, each layer having a different density. The multi-layer fabric can be used as a reinforced absorbable hemostat medical device.

12 Claims, No Drawings

REINFORCED ABSORBABLE MULTI-LAYERED FABRIC FOR HEMOSTATIC APPLICATIONS

FIELD OF THE INVENTION

The present invention relates to a reinforced absorbable multi-layered hemostat that is useful as a construct for use as a medical device.

BACKGROUND OF THE INVENTION

The control of bleeding is essential and critical in surgical procedures to improve the outcomes and to shorten the duration of the surgery in the operating room. Several hemostatic materials including oxidized cellulosic based material has been used as a dressing in a variety of surgical procedures, including neurosurgery, abdominal surgery, cardiovascular surgery, thoracic surgery, head and neck surgery, pelvic surgery and skin and subcutaneous tissue procedure.

It is generally accepted to use multilayered fabrics in connection with medical procedures. For example, multilayered fabrics are used as all purpose pads, wound dressings, surgical meshes, including hernia repair meshes, adhesion prevention meshes and tissue reinforcement meshes, defect closure devices, and hemostats.

U.S. Pat. No. 5,593,441 to Lichtenstein et al describes a composite prosthesis preferably having a sheet of polypropylene mesh that allows tissue in-growth, such as Marlex® mesh. This reference discloses that other surgical materials that are suitable for tissue reinforcement and defect closure may be utilized, including absorbable meshes such as a polyglactin 910 (Vicryl®) mesh. The composite prosthesis of Lichtenstein et al also has an adhesion barrier, preferably a sheet of silicone elastomer.

U.S. Pat. No. 5,686,090 to Schilder et al describes the use of a fleece in combination with a nonabsorbable or absorbable film to prevent mis-growths to adjacent tissue and to reduce adhesions. Schilder et al generally discloses that polypropylene, polyester, polyglactin, polydioxanone or poliglecaprone 25 may be used as the fleece material or the film material.

Published U.S. Patent Application 2006/00084930, to Dhanaraj et al, describes a reinforced absorbable multilayered fabric that can be used in medical devices specifically for tissue engineering applications. The matrix comprises first preparing a repair site for implantation, and then disposing the reinforced absorbable multilayered fabric at site. The first absorbable nonwoven fabric comprises fibers comprising aliphatic polyester polymers, copolymers or blends thereof; while the second absorbable woven or knitted fabric comprises oxidized regenerated cellulose fibers.

U.S. Pat. No. 4,626,253 to Broadnax et al, describes a device that relates to a surgical hemostat for control of bleeding, and more particularly, to a knitted fabric of oxidized cellulose having superior handling and hemostatic properties.

U.S. Pat. No. 7,666,803 to Shetty et al, describes the method of making or reinforced absorbable multilayered fabric that can be used as a hemostat. The matrix comprises first preparing a repair site for implantation, and then disposing the reinforced absorbable multilayered fabric at site. The first absorbable nonwoven fabric comprises fibers comprising aliphatic polyester polymers, copolymers or blends thereof; while the second absorbable woven or knitted fabric comprises oxidized regenerated cellulose fibers. The method also describes the appropriate densities and thickness that can be used to make the matrix in that particular invention.

None of the above references describes or suggests a reinforced absorbable multi-layer of nonwoven fabric with each layer having different densities. Furthermore, none of the above references describes or suggests this nonwoven dual-layered fabric having hemostasis function.

SUMMARY OF THE INVENTION

The present invention is directed to a synthetic fabric comprising a non-woven matrix having at least two layers of a first absorbable staple of a polyglycolide/polylactide copolymer and a second absorbable staple of a polyglycolide/polylactide copolymer, where the first absorbable fabric is compacted to a density of about 60 mg/cc and the second absorbable fabric is compacted to a density of about 120 mg/cc. The first and second absorbable fabrics can consist of a copolymer of glycolide/lactide at a 90/10 mol/mol composition. The first and second absorbable fabrics can comprise staples having a length from about 0.75 to 2.5 inches and/or can be derived from about 1 to 4 denier per filament. The fabric staples can be crimped. The first absorbable fabric and second absorbable sheet can be needle-punched into each other to secure a nonwoven fabric matrix.

In one embodiment, the first absorbable fabric is compacted to a thickness of about 0.5 mm to about 1.5 mm, more preferably about 1 mm. Alternatively, the second absorbable fabric can be compacted to a thickness of about 0.75 mm to 3 mm, more preferably about 1 mm. In one embodiment, the synthetic fabric, particularly as a dual-layer matrix, can be used a medical device, such as a hemostatic device.

DETAILED DESCRIPTION OF THE INVENTION

The present invention is a synthetic fabric having at least two non-woven layers, each layer consisting essentially of a blend of staples from copolymers of polyglycolide and polylactide fibers and each layer having a different density that can be used as a reinforced absorbable multi-layered, preferably dual-layered, hemostat device. In one embodiment, the hemostatic device is substantially free of any oxidized polysaccharide material. While oxidized polysaccharide materials, such as oxidized regenerated cellulose, are known for use as a hemostat, the presence of the ORC can be detrimental to the stability of biologically active hemostatic agents, can reduce the activity levels of the biological active hemostatic agents in the vicinity of a wound by decreasing the pH in this region, and generally degrade faster after placement on an injury.

One method for preparing the inventive matrix begins by melt-spinning poly (glycolide-co-lactide) into a PGLA copolymer fiber. A multi-filament yarn based on the PGLA copolymer fibers can be consolidated, crimped and cut into staples having a length of 2.0 inches. The staples can then be carded to create a nonwoven batt and compacted to a thickness of about 1.0 mm and a density of about 60 mg/cc. A second nonwoven batt can be created by following substantially the same procedures for melt-spinning, consolidating, crimping, cutting, carding and compacting to a thickness of about 1.0 mm and a density of about 120 mg/cc. Two nonwoven fabric materials prepared as described above with a first density of 60 mg/cc and a second density of 120 mg/cc precisely were laid onto each other and firmly attached via 2 passes in the needlepunching equipment. The multilayered fabric was trimmed and scoured in 3 discrete isopropyl alcohol baths to remove spin finish and any machine oils. The scoured multilayered fabric was dried in an oven at 70° C. for 30 minutes, cooled and weighed. Then the needle-punched multi-layer nonwoven fabric matrix is suitable for use as a hemostatic device.

One method of making the fabric described herein is by the following process. Absorbable polymer fibers, having a size of denier per fiber of about 1 to 4, can be consolidated to about 80 to 120 denier multifilament yarn and then to about 800 to 1200 denier yarn, thermally crimped and then cut to staple having a length between about 0.75 and 2.5 inch. The staples can be fed into a multi-roller dry lay carding machine one or more times and carded into a uniform nonwoven batt, while humidity is controlled to between about 20-60% at a room temperature of 15 to 24° C. For example, the uniform nonwoven batt can be made using a single cylinder roller-top card, having a main cylinder covered by alternate rollers and stripper rolls, where the batt is doffed from the surface of the cylinder by a doffer roller and deposited on a collector roll. The batt may be further processed via needlepunching or any other means such as calendaring. Thereafter, the first absorbable nonwoven fabric may be attached to the second absorbable woven or knitted fabric by various techniques such as needlepunching. The reinforced absorbable fabric can then be scoured by washing in an appropriate solvent and dried under mild conditions for 10-30 minutes.

The fabric is scoured using solvents suitable to dissolve any spin finish. Solvents include, but are not limited to, isopropyl alcohol, hexane, ethyl acetate, and methylene chloride. The fabric is then dried under conditions to provide sufficient drying while minimizing shrinkage.

The multi-layer, non-woven hemostatic matrix described herein provides and maintains effective hemostasis when applied to a wound requiring hemostasis. Effective hemostasis, as used herein, is the ability to control and/or abate mild to moderate bleeding within an effective time, as recognized by those skilled in the art of hemostasis. Further indications of effective hemostasis may be provided by governmental regulatory standards and the like. Examples of mild to moderate bleeding include, without limitation, bleeding due to spleen resection, liver resection, blunt liver trauma, and blunt spleen trauma.

The multi-layer, non-woven hemostatic matrix described above can include one or more hemostatic agents. Hemostatic agents, for purposes of this application, are agents that have a hemostatic effect, more preferably, slow, impede and eventually stop bleeding at the site of their application. One method for producing a hemostatic effect at the site of an injury is to introduce one or more agents found in the blood clotting cascade process that may react with one another or other agents naturally present in the body. Thrombin, for example, can be used for producing a hemostatic effect in one embodiment, while in another embodiment, thrombin and fibrinogen are used together to produce the desired hemostatic effect. Additional components, such as calcium, can also be provided to further enhance the hemostatic effect of the thrombin and/or fibrinogen.

In one embodiment, the multi-layer, nonwoven hemostatic matrix retains solid thrombin and/or solid fibrinogen in powdery, particulate form without separation and with minimal loss of the powder from its surface due in part to the means for the addition of the hemostatic agent(s) and the non-woven nature of the matrix. Additionally, due to the different layer densities, the hemostatic agents are not dispersed evenly throughout the matrix such that greater hemostatic agent is present in the relatively low density non-woven layer, which is placed on the injury site. In a preferred method for applying thrombin and/or fibrinogen to the matrix, one or more biologics containing solutions are separately lyophilized. The lyophilized materials are then ground into powders using a superfine mil, ball milled or a cooled blade mill. The powders are weighed and suspended together in a carrier fluid in which the proteins are not soluble. A preferred carrier fluid is a perfluorinated hydrocarbon, including but not limited to HFE-7000, HFE-7100, HFE-7300 and PF-5060 (commercially available from 3M of Minnesota). Any other carrier fluid in which the proteins do not dissolve may be used, such as alcohols, ethers or other organic fluids. The suspension is thoroughly mixed and applied to the absorbable nonwoven fabric via conventional means such as wet, dry or electrostatic spraying, dip coating, painting, or sprinkling, while maintaining a room temperature of about 15 to 24° C. and relative humidity of about 10 to 60%, preferably no more than 30%. The multi-layer non-woven matrix is then dried at ambient room temperature and packaged in a suitable moisture barrier container. The hemostatic dressing having the thrombin and/or fibrinogen contains no more than 25% moisture, preferably no more than 15% moisture, and most preferably no more than 5% moisture.

The thrombin and/or fibrinogen may be animal derived, human, or may be recombinant. The thrombin activity on the dressing may be in the range of about 20 to 500 $IU/cm^2$, preferably about 20 to 200 $IU/cm^2$, and most preferably about 50 to 200 $IU/cm^2$. The fibrinogen activity on the dressing may be in the range of about 2 to 15 $mg/cm^2$, preferably about 3 to 12 $mg/cm^2$, and most preferably about 5 to 10 $mg/cm^2$. The amount of thrombin and/or fibrinogen powder is preferably applied to the nonwoven fabric in a sufficient amount to cover its surface such that no area is visibly devoid of coverage. The powder may sit mostly on top of the nonwoven fabric or, more preferably penetrates into the nonwoven fabric.

As a surgical dressing, the hemostatic matrix described herein can be used as an adjunct to primary wound closure devices, such as arterial closure devices, staples, and sutures, to seal potential leaks of gasses, liquids, or solids as well as to provide hemostasis. The matrix of the present invention is particularly advantageous due to the improved tensile strength, especially relative to hemostatic matrix made from or containing one or more layers of cellulosic materials, such as oxidized regenerated cellulose. For example, the dressing can be utilized to seal air from tissue or fluids from organs and tissues, including but not limited to, bile, lymph, cerebrospinal fluids, gastrointestinal fluids, interstitial fluids and urine.

The hemostat described herein has additional medical applications and may be used for a variety of clinical functions, including but not limited to matrix/substrate, i.e., fibrinogen/thrombin coating, tissue reinforcement, and buttressing, i.e., for gastrointestinal or vascular anastomoses, approximation, i.e., to connect anastomoses that are difficult to perform (i.e. under tension), and tension releasing. The hemostat matrix may additionally promote and possibly enhance the natural tissue healing process in all the above events. This dressing can be used internally in many types of surgery, including, but not limited to, cardiovascular, peripheral-vascular, cardio-thoracic, gynecological, neuro- and general surgery. The hemostat may also be used to attach medical devices (e.g. meshes, clips and films) to tissues, tissue to tissue, or medical device to medical device.

EXAMPLE 1

Dual-Layer Matrix of PGLA

Poly (glycolide-co-lactide) (PGLA, 90/10 mol/mol) is melt-spun into a PGLA copolymer fiber. A multi-filament yarn from the PGLA copolymer fiber is consolidated, crimped and cut into staple having a length of 2.0 inches. The staple is carded to create a nonwoven batt and then compacted to a thickness of about 1.0 mm and a density of about 60 mg/cc. A second nonwoven batt is created by the similar procedures and then compacted to a thickness of about 1.0 mm and a density of about 120 mg/cc. Two nonwoven fabrics with a density of 60 mg/cc and 120 mg/cc are then needle-punched into each other to secure the nonwoven dual layer matrix.

EXAMPLE 2

Dual-Layer Matrix Achieved Hemostasis in Spleen Model

A mild to moderate bleeding model is created by making an incision of 15 mm long and 3 mm deep on a swine spleen. A dual-layer matrix as described in Example 1 is then applied to the surgical site and tamponade is applied for two minutes. Hemostasis is checked for 30 seconds after the two-minute tamponade. If free flow bleeding is not observed within 30 seconds, the time to hemostasis is noted. If free flow bleeding is observed, a 30-second tamponade is reapplied until hemostasis is achieved or until the testing period reaches ten minutes, which is defined as a failure in hemostasis. Three test samples cut to a size of 2.5×4.0 centimeters of the dual-layer matrix prepared in accordance with Example 1 achieved hemostasis at 5.62±0.76 minutes (Table 1).

TABLE 1

Hemostasis of PGLA dual-layer matrix in spleen model

| | Sample # | | | | |
|---|---|---|---|---|---|
| | 1 | 2 | 3 | Mean | SD |
| Hemostasis (min) | 5.12 | 5.25 | 6.50 | 5.62 | 0.76 |

EXAMPLE 3

The mechanical property of dual-layer matrix prepared according to Example 1 is characterized using an in-vitro test. The dual-layer matrix is cut into strips (approximately ⅜ inch wide by 2 inches long). The tensile strength of the dual-layer matrix is then evaluated at dry and wet conditions by using an Instron Tensile Analyzer. At the wet conditions, strips are placed in a conical tube containing PBS buffer at a pH of 7.4 at 37° C. The tensile strength of the strips is then measured at 90 minutes, 4 days, 7 days, 11 days, and 14 days. The measured values for tensile strength for the strips of dual-layer matrix are shown in Table 2.

TABLE 2

Tensile strength of Dual-Layer Matrix in dry and wet conditions

| | Dry | 90 min | 4 days | 7 days | 11 days | 14 days |
|---|---|---|---|---|---|---|
| Tensile Strength (Newton/cm) | 119.8 ± 10.6 | 114.9 ± 9.7 | 91.2 ± 11.6 | 51.8 ± 3.2 | 29.4 ± 3.5 | 15.7 ± 1.5 |

We claim:

1. A synthetic fabric comprising a non-woven matrix having at least two layers of a first absorbable staple of a polyglycolide/polylactide copolymer and a second absorbable staple of a polyglycolide/polylactide copolymer, where the first absorbable fabric is compacted to a density of about 60 mg/cc and the second absorbable fabric is compacted to a density of about 120 mg/cc.

2. The synthetic fabric of claim 1, where the first and the second absorbable fabrics consist of a copolymer of glycolide/lactide at a 90/10 mol/mol composition.

3. The synthetic fabric of claim 1, where the first and the second absorbable fabrics comprise of staples having a length from about 0.75 to 2.5 inches.

4. The synthetic fabric of claim 3, where the staples are crimped.

5. The synthetic fabric of claim 4, where the first absorbable fabric is compacted to a thickness of about 0.5 mm to about 1.5 mm.

6. The synthetic fabric of claim 5, where the second absorbable fabric is compacted to a thickness of about 0.75 mm to 3 mm.

7. The synthetic fabric of claim 5, where one sheet of the first absorbable fabric and one sheet of the second absorbable sheet are needle-punched into each other.

8. The synthetic fabric of claim 7 wherein the fabric further comprises at least one hemostatic agent.

9. The synthetic fabric according to claim 8 wherein the fabric further comprises fibrinogen and thrombin as the hemostatic agent.

10. The synthetic fabric according to claim 9 wherein the fibrinogen and thrombin are provided on the fabric as lyophilized powders.

11. The synthetic fabric according to claim 10 wherein the lyophilized powders are dispersed unevenly as measured from the outer surface of the first layer to the outer surface of the second layer.

12. The synthetic fabric according to claim 1 wherein strips of from about ⅜ inch wide to about 2 inches long have measured tensile strengths (Newton/cm) as measured in an Instron Tensile Analyzer of:
   a. about 120 in dry condition;
   b. about 115 in wet condition for 90 minutes;
   c. about 90 in wet condition for 4 days;
   d. about 52 in wet condition for 7 days;
   e. about 29 in wet condition for 11 days or;
   f. about 16 in wet condition for 14 days.

* * * * *